US005688907A

United States Patent [19]
Wood et al.

[11] Patent Number: 5,688,907
[45] Date of Patent: Nov. 18, 1997

[54] POLYMERS OF MALEIC ACID WITH AMINES

[75] Inventors: Louis L. Wood, Rockville; Gary J. Calton, Elkridge, both of Md.

[73] Assignee: SRCHEM, Inc., Elkridge, Md.

[21] Appl. No.: 445,643

[22] Filed: May 22, 1995

Related U.S. Application Data

[62] Division of Ser. No. 132,246, Oct. 6, 1993, Pat. No. 5,442,038.

[51] Int. Cl.$^6$ .............................. C08G 69/10; C08G 73/00
[52] U.S. Cl. .......................... 528/363; 528/328; 525/419; 525/420
[58] Field of Search ...................................... 528/328, 363; 525/419, 420

[56] References Cited

U.S. PATENT DOCUMENTS

| | | | |
|---|---|---|---|
| 5,219,952 | 6/1993 | Koskan et al. | 525/419 |
| 5,296,578 | 3/1994 | Koskan et al. | 528/363 |
| 5,393,868 | 2/1995 | Freeman et al. | 528/480 |
| 5,519,110 | 5/1996 | Wood et al. | 528/363 |

*Primary Examiner*—P. Hampton-Hightower
*Attorney, Agent, or Firm*—William S. Ramsey

[57] ABSTRACT

Polymers of maleic acid may be prepared by thermally polymerizing malic acid, maleic acid or fumaric acid with less than one equivalent of ammonia. The polymers are modified by the incorporation of amines, carboxylic acids or combinations thereof. The polymers formed are excellent inhibitors of alkaline earth salt deposition, dispersants, tartar control additives, detergent additives, and water treatment agents.

3 Claims, No Drawings

POLYMERS OF MALEIC ACID WITH AMINES

This application is a division of application Ser. No. 08/132,246, filed Oct. 6, 1993, now U.S. Pat. No. 5,442,038.

FIELD OF THE INVENTION

This invention relates to polymers of maleic acid and amines.

DESCRIPTION OF RELATED ART

It is well known that polymers of ammonia and maleic acid can be prepared by thermal condensation of one or more equivalents of ammonia with maleic acid, malic acid, fumaric acid or the mono- or diamides of maleic acid, malic acid or fumaric acid.

U.S. Pat. No. 4,839,461 discloses a method for making polyaspartic acid from maleic acid and ammonia by reacting these constituents in a 1:1–1.5 molar ratio by raising the temperature to 120°–140° C. over a period of 4–6 hours and maintaining it for 0–2 hours.

Dessaigne (Comp. rend. 31, 432–434 [1850]) prepared condensation products which gave aspartic acid on treatment with nitric or hydrochloric acid by dry distillation of the acid ammonium salts of malic fumaric or maleic acid at unspecified times and temperatures.

U.S. Pat. No. 3,846,380 discloses that polysuccinimide may be made by heat condensation of the following starting materials, aspartic acid; ammonium salts of aspartic acid, malic acid, maleic acid and fumaric acid; and mono- and diamides of aspartic acid, malic acid, maleic acid and fumaric acid.

U.S. Pat. No. 4,696,981 discloses the formation of anhydropolysuccinic acid by the microwave radiation of ammonium salts of malic acid via the formation of ammonium maleate.

Jpn. Kokai 60,203,636 [C.A. 104, 207690m, 1986] discloses a method for the synthesis of copolymers of aspartic acid by heating amides, ammonium salts or monoamide-ammonium salts of malic acid, maleic acid or/and fumaric acid with one or more amino acids at 180° C. for four hours.

A method of preparation of polyaspartate, useful for inhibition of incrustations due to materials causing hardness in water and of value in detergent formulations, in which maleic acid or fumaric acid are reacted in a molar ratio of 1:1–2.1 at temperatures greater than 190° C., followed by conversion of the polymer formed in this reaction to a salt of polyaspartic acid by basic hydrolysis is disclosed by U.S. patent application Ser. No. 08/007,376, filed May 14, 1992, by Louis L Wood.

A method for obtaining higher molecular weight copolymers of polyaspartic acid, suitable for the inhibition of scale deposition, by reacting maleic acid and ammonia in a stoichiometric excess, with a diamine or a triamine, at 120°–350° C., preferably 180°–300° C., and then converting the copolymer of polysuccinimide formed to a salt of a copolymer of polyaspartic acid by hydrolysis with a hydroxide is disclosed in U.S. patent application Ser. No. 07/968,506, filed Oct. 10, 1992 by Louis L. Wood.

Copolymers of polyamino acids formed by reaction of polysuccinimide with alkyl, alkenyl, aromatic amines or alkyl and alkenyl polyamines are useful as inhibitors of mineral scale deposition are disclosed in U.S. patent application Ser. No. 07/968,319, filed Oct. 29, 1992 by Louis L. Wood and Gary J. Calton.

U.S. patent application Ser. No. 07/994,922, filed Dec. 22, 1992, by Louis L. Wood and Gary J. Calton, discloses copolymers of polyaspartic acid which are suitable for the inhibition of scale deposition which are obtained by reacting maleic acid, an additional polycarboxylic acid and ammonia in a stoichiometric excess, at 120°–350° C., preferably 180°–300° C., to provide copolymers of polysuccinimide. In a second embodiment, a polyamine was added to the reaction mix. These intermediate polysuccinimide copolymers could then be converted to the salts of copolymers of polyaspartic acid by hydrolysis with a hydroxide.

U.S. patent application Ser. No. 08/031,856, filed Mar. 16, 1993 by Louis L. Wood, discloses a method for preparing copolymers of polyamino acids by reaction of an alcohol with maleic anhydride to form the half ester followed by addition of ammonia, ammonia and an amine, or ammonia and a polyamine. The mixture is then heated to 120°–350° C. to form polysuccinimide or a derivative thereof. The resulting polysuccinimide may be hydrolyzed to form its salt or reacted further to provide a derivative of polyaspartic acid.

It is also well known that maleic polymers can be obtained through radical polymerization as disclosed in U.S. Pat. No. 5,064,563 and references cited therein.

SUMMARY OF THE INVENTION

We have found that useful polymers and salts thereof can be prepared by thermal condensation, at temperatures above 120° C., but preferably above 160° C. and more preferably above 190° C. for a time sufficient to remove the water of condensation, of less than one equivalent of an amine having the formula NHR'R" where R' and R" can be the same or different and where R' and R" independently represent hydrogen or an alkyl, a carboxy alkyl, an hydroxyalkyl, an alkenyl, an alkyl amine, or an alkyloxy amine, with a monomer selected from the group of monomers consisting of maleic acid, malic acid, fumaric acid or maleic anhydride. Such polymers are easily formed when the amine is present at 0.05 equivalent of amine per mole of monomer to less than 1 equivalent of amine per mole of monomer. A preferred range of amine is 0.25 to less than 1 equivalent of amine per mole of monomer. An especially preferred range of amine is 0.5 to less than 1 equivalent of amine per mole of monomer. Amines such as ammonia or those having at least one primary or secondary amine are useful in formation of the polymers. Molecules having additional amine groups consisting of at least one or more primary or secondary amines are of value in extending the molecular weight of the polymer. Illustrative of the types of amines which might be used are alkyl amines having 1–36 carbons, polyoxyalkyleneamines, polyoxyalkylenediamines, polyoxyalkylenetriamines, alkyl diamines such as ethylene diamine or hexanediamine, alkyltriamines such as diethylene triamine or melamine, or amino acids such as lysine and arginine. Permutations and combinations of the various amines provide polymers, all of which have useful properties, to a greater or lesser degree, as described below. The process for synthesis of the polymers comprises polymerizing (1) one of the members of the group consisting of maleic acid, malic acid, and fumaric acid and (2) less than one equivalent of ammonia, at a temperature greater than about 120° C., to produce said polymer; polymerizing (1) one of the members of the group consisting of maleic acid, malic acid, and fumaric acid, (2) less than one equivalent of ammonia and (3) an amine, at a temperature greater than about 120° C., to produce said polymer; polymerizing (1) one of the members of the group consisting of maleic acid, malic acid, and fumaric acid, (2) less than one equivalent of ammonia, and (3) a carboxylic acid, at a temperature greater than about 120° C., to produce said polymer; or polymerizing (1) one of the members of the group consisting of maleic acid, malic acid, and fumaric acid, (2) less than one equivalent of ammonia, (3) an amine and (4) a carboxylic acid, at a temperature greater than about 120° C., to produce said polymer. The polymer may be hydrolyzed to form a salt having high carboxyl functionality by further reacting said polymer with a salt of an alkali, an alkaline earth metal or ammonia which is capable of hydrolyzing said polymer. Among those salts capable are the oxides, carbonates or other weak acid salts, such as those of organic acids, and hydroxides of the alkali or alkaline earth elements, or ammonium hydroxide. Each of these hydrolysates provides a salt of the polymer wherein the counter-ion of the salt is an ion of an alkali, an alkaline earth metal or ammonia. Other carboxylic acids may be incorporated providing a variation in the hydrophobic/hydrophilic ratio and varying the interatomic distance between carboxylic acid functionalities. Illustrative examples of such acids are monocarboxylic acids such as alkyl carboxylic acids containing 1–36 carbons, for example stearic, oleic, N-methyl-N-lauric, and palmitic acids, amino acids such as alanine, lysine and polycarboxylic acids such as adipic acid, citric acid, fumaric acid, malic acid, malonic acid, succinic acid, glutaric acid, oxalic acid, pimelic acid, itaconic acid, nonanedioic acid, dodecanedioic acid, octanedioic acid, isophthalic acid, terphthalic acid, phthalic acid or polycarboxylic acids, such as aspartic acid or glutamic acid. The molecular weight of these polymers, with or without the inclusion of alternate carboxylic acids, may be extended by substituting a polyamine for a portion of the ammonia used.

The polymer formed may then be hydrolyzed to give a water soluble polycarboxylic acid salt. The alkaline hydrolysis is carried out for a suitable time at a temperature in the range of 0° to 50° C., and if necessary, with cooling. The reaction is generally complete after several minutes, but it may take several hours, in some cases, before it goes to completion. The alkali hydroxides or carbonates of alkali metals and alkaline earth metals, for example, NaOH, KOH, LiOH, RbOH, CsOH, $Li_2CO_3$, $Na_2CO_3$, $Rb_2CO_3$, $Cs_2CO_3$, $Ba(OH)_2$, etc., may be employed as well as the salts of the alkali or alkaline earth metals with a weak Lewis acid, where the pH of the salt in aqueous solution is above 5.5. Illustrative examples of these salts are the sodium salts of carbonic acid, acetic acid, formic acid and the like. The concentration of alkali employed can be varied widely depending upon the number of hydrophobic groups in the material to be hydrolyzed, but the preferred concentration is in the range of 0.1 to 10N. The hydrolysis product may provide both alpha and beta carboxyl groups to the amines. This ratio may vary due to the strength of the hydrolyzing agent; however all of the hydrolyzing agents tested have given excellent activities in the testing carried out.

At the present time, the structure of the polymers is unknown, and although not wishing to be held to any theory, the lack of an equivalent amount of an amine in the reaction with maleic acid would appear to preclude the formation of a strict polyamide, as has been suggested to occur by a number of authors concerning the thermal polymerization of maleic acid with more than one equivalent of an amine. Studies of the mechanism of the anionic polymerization of maleic anhydride catalyzed by triphenyl phosphine and tributyl phosphine, showed the formation of succinic anhydride units and cyclopentanone units or ketoolefinic units. Such units, along with their nitrogen containing analogs may well present in the polymer of the present invention, most probably randomly interspersed in the polymer chain.

The polymers of the present invention provide properties which are different from their counterparts prepared with one or more equivalents of amine. The polymers also provide materials which are distinctly advantageous in their lighter color. The economic advantage due to reduced quantities of ammonia provides an economic incentive for their use.

The polymers are valuable intermediates which may be reacted further, for instance, after the manner of Jacquest, et al, U.S. Pat. No. 4,363,797, Fujimoto et al, U.S. Pat. No. 3,846,380 or Wood, U.S. patent application Ser. No.08/031,856.

The salts of these polymers are valuable as solubilizing agents, dispersing agents, emulsifying agents, rust-proofing agents, fiber-treating agents, level dyeing agents and retarding agents, inhibitors of metal scale deposition and inhibitors of corrosion of ferrous metals. As dispersing agents, they are useful in suspending paints, coal, clay, pigments and paper fibers, to provide even suspensions, pumpable fluids and to prevent settling of sediments, for instance. The inhibition of metal scale deposition by these polymer salts may occur by prevention of nucleation of salts such as those of calcium, strontium, barium and magnesium in waters as well as by prevention of crystal growth by the addition effective amount of a the salt of the polymers. The use of said polymer salts in water treatment may also be desirable as a result of disruption of the crystal pattern of the metal salt, making a scale which is more easily removed. Thus, the incorporation of these salts or polymers into water treatment composition, which include a scale deposition inhibition effective amount of the salt, or polymer which may be hydrolyzed in situ, provides an effective water treatment composition. These polymer salts are useful when incorporated into laundry and dishwashing detergents as suspending agents or to prevent metal salt deposition on clothing, glassware or metal objects. The salts may be incorporated in oral health care products to prevent the accumulation of tartar on the teeth or on porcelain objects used in the mouth. Zinc salts are very useful in oral health care. They are especially useful in dentrifice compositions for inhibition of tartar deposition in effective amount of the salts of the polymers in combination with an orally acceptable dentrifice composition compatible with said salt, and more especially in the form of an oral hygiene formulation such as mouthwashes, rinses, irrigating solutions, abrasive gel dentrifices, nonabrasive gel dentrifices, denture cleansers, coated dental floss, interdental stimulator coatings, chewing gums, lozenges, breath fresheners, foams and sprays. They are useful in treating cloth and fibers as warp sizing compounds.

The addition of the polymer itself to the detergent formulation may be desirable where the pH of the detergent is sufficient to cause hydrolysis of the polymer yielding the salt in situ.

One object of this invention is to provide novel compositions useful as solubilizing agents, dispersing agents, emulsifying agents, rust-proofing agents, fiber-treating agents, level dyeing agents and retarding agents, inhibitors of scale deposition, inhibitors of corrosion of ferrous metals, inhibitors of scale formation in hard water, boiler water, cooling water, oil well waters, agricultural sprays and irrigation water and as builders and dispersants in detergent formulations.

Another object is to provide a method of producing these novel polymers.

Yet another object is to provide compositions suitable for incorporation in oral health care products for the inhibition of dental calculus.

A final object is to provide methods for preventing scale formation which are effective, low in cost, and environmentally benign.

DETAILED DESCRIPTION OF THE EMBODIMENTS

EXAMPLE 1

A solution of 39.2 g (0.4 moles) of maleic anhydride in 40 ml of water were stirred at 25°–75° C. for 45 min to give a white slurry of maleic acid. To this slurry was added 42 g of 30% aqueous ammonium hydroxide (0.36 moles $NH_3$, 90% of theoretical required) with stirring and cooling. The resultant clear solution was then tumbled at 180°–200° C. (salt bath temperature) for 10 min to give a tan solid. The solids were pulverized and tumbled for 10 min at 200°–225° C. Once again the solids were pulverized and then tumbled at 225°–240° C. for 10 min. Finally, the solids were pulverized and tumbled for 10 min at 230°–240° C. to give 39.3 g of tan powder which was insoluble in water.

EXAMPLE 2

The procedure of Example 1 was repeated using 35 g of 30% aqueous ammonium hydroxide (0.3 moles $NH_3$, 75% of theoretical required) to give 39.3 g of pink-tan powder which was insoluble in water.

EXAMPLE 3

The procedure of Example 1 was repeated using 23.5 g of 30% aqueous ammonium hydroxide (0.2 moles $NH_3$, 50% of theoretical required) to give 37.8 g of pink-tan powder which was insoluble in water.

EXAMPLE 4

The procedure of Example 1 was repeated using 11.6 g of 30% aqueous ammonium hydroxide (0.1 moles $NH_3$, 25% of theoretical required) to give 36.3 g of pink-tan powder which was soluble in water.

EXAMPLE 5

Four gram portions of the solids from Examples 1–4 were each dissolved 9.0 g of water containing 1.25 g of NaOH to give clear red-brown solutions, pH 7.5–8.5, estimated to contain 36–37% solids. Gel permeation chromatography (GPC) was run on a 1 cm×18 cm, Sephadex G-50 column in a mobile phase of 0.02 M sodium phosphate buffer, pH 7.0, running at 0.5 ml/min, with detection in the UV at 240 nm. Table 1 shows the results which were obtained.

TABLE 1

| Sample | Residence time (min) |
| --- | --- |
| Example 1 | 21.5 |
| Example 2 | 21.0 |
| Example 3 | 23.0 |
| Example 4 | 31.0 |

EXAMPLE 6

Preparation of a maleic polymer with a polyamine

To a solution of 4.6 g (0.025 moles) of lysine in 40 g of water containing 1.0 g of NaOH was added 39.2 g (0.4 moles) of maleic anhydride while stirring at 70°–75° C. for 10 min to give a pale yellow slurry of maleic acid. To this slurry was added 5.0 g (0.29 moles) of anhydrous ammonia with stirring and cooling. This solution was then treated with heat as in Example 1 to give 44.0 g of pink-tan powder which was insoluble in water.

A 4.0 g portion of the powder was dissolved in a solution of 9.0 g of water containing 1.3 g of NaOH to give a clear red-brown solution, estimated to contain 36% solids. Addition of 0.55 g of 30% $H_2O_2$ gave a clear yellow solution after 16 hrs at 25° C. Chromatography of this solution as in Example 5 gave a peak centered at 13 min.

To prepare a 100% ammonia sample for comparison purposes, this experiment was carried out in the proportions above except that 1 equivalent of ammonia was used (noted as 6a in the results).

EXAMPLE 7

Calcium sulfate inhibition assay

The material to be tested as an inhibitor of calcium sulfate scale formation was added in the quantities indicated to a solution of 10 ml of calcium chloride solutions 17.3 g of $CaCl_2$ dihydrate in 800 g of water containing 33 g of NaCl). To this solution was then added 10 ml of sulfate solution (16.8 g of $Na_2SO_4$ and 33 g NaCl in 800 ml of water). The mixture was then sealed and maintained at 65° C. for 16 hours. Finally the mixture was filtered through Whatman #2 paper and dried at 65° C. for 8 hours, after which the weight of precipitate was determined. The results in Table 2 were obtained.

TABLE 2

| | percent of | $CaSO_4$ Inhibition of Precipitation | |
| --- | --- | --- | --- |
| Sample from Example Number | equivalence of ammonia | 0 ppm | 1.25 ppm (mg ppt) | 2.5 ppm (mg ppt) |
| blank | | 79.5 | | |
| 1 | 90 | | 23 | 10 |
| 2 | 75 | | 4.5 | 1 |
| 3 | 50 | | 48 | 0 |
| 4 | 25 | | 51 | 35 |
| a | 100 | | 37 | 19 |
| 6 | 75 | | 49 | 28 |
| 6a | 100 | | 52 | 14 |
| polyaspartic acid | | | 38 | 10 |

*prepared by the method of Example 1 using 1 equivalent of ammonia

EXAMPLE 8

Inhibition of calcium carbonate precipitation by the calcium drift assay

In this assay a supersaturated solution of calcium carbonate is formed by adding 29.1 ml of 0.55 M NaCl and 0.01 M KCl to 0.3 ml of 1.0 M $CaCl_2$, 5 microliter of sample (100 mg of the aqueous solution in 10 ml of water) and 0.6 ml of 0.5 M $NaHCO_3$. The reaction is initiated by adjusting the pH to 8.55–8.65 by titration with 0.5N NaOH. At three minutes, 10 mg of $CaCO_3$ is added and the pH is recorded. The decrease in pH is directly correlated to the amount of $CaCO_3$ that precipitates. The additive concentration in the final test solution is 2.7 ppm.

TABLE 3

| Sample from Example Number | percent of equivalence of NH$_3$ | CaCO$_3$ Drift (pH units) |
|---|---|---|
| blank | | 1.05 |
| 1 | 90 | 0.60 |
| 2 | 75 | 0.63 |
| 3 | 50 | 0.53 |
| 4 | 25 | 1.05 |
| a | 100 | 0.88 |
| 6a | 100 | 0.60 |
| polyaspartate | | 0.44 |
| 2000 mol. wt. polyacrylate | | 0.37 |
| 4500 mol. wt. polyacrylate | | 0.20 |

*prepared by the method of Example 1 using 1 equivalent of ammonia

EXAMPLE 9

Dispersant activity

Kaolin dispersion was run by placing the sample (final concentration of 20 ppm) in a 12×100 mm test tube containing 5 ml of deionized water and adding 40,000 ppm kaolin clay. The height of the suspended solids was measured and compared to a control in which no dispersant had been added. A higher value indicates better dispersancy. Table 4 gives the results.

TABLE 4

| Sample from Example Number | percent of equivalence of NH$_3$ | Kaolin clay height (mm) suspension | settled |
|---|---|---|---|
| blank | | 0 | 15 |
| 1 | 90 | | |
| 2 | 75 | 47 | 3.5 |
| 3 | 50 | 48 | 2.5 |
| 4 | 25 | 48 | 2.5 |
| a | 100 | 50 | 3 |
| 6a | 100 | | |
| polyaspartate | | | |
| 2000 mol. wt. polyacrylate | | 48 | 2 |
| 4500 mol. wt. polyacrylate | | 48 | 3 |

*prepared by the method of Example 1 using 1 equivalent of ammonia

EXAMPLE 10 pH drift assay for calcium phosphate

A solution which is supersaturated with calcium phosphate was prepared by adding 0.1 ml of previously prepared aqueous solutions of 1.32 M CaCl$_2$ dihydrate and 0.90 M Na$_2$PO$_4$ to 29.8 ml of distilled water, resulting in 4.4 mM Ca$^{2+}$ and 3.0 mM dissolved inorganic phosphorus. The reaction vessel is maintained at 25° C. There is considerable irregularity in the time necessary to begin precipitation. Calcium phosphate begins to crystalize within a few minutes of initiation (first drop in pH) and is transformed to hydroxyapatite, Ca$_{10}$(PO$_4$)$_6$(OH)$_2$, with a consequent downward pH drift (second drop in pH). The reaction ceases when the reactants are depleted and the pH ceases its downward drift. The samples prepared in Examples 1–4 and 6 were tested and the results (the average of two separate runs) are given in Table 5.

TABLE 5

| Sample from Example Number | percent of equivalence of ammonia | Induction period (min) |
|---|---|---|
| blank | | 17.5 |
| | 100 | 34.5 |
| 1 | 90 | 30.5 |
| 2 | 75 | 41 |
| 3 | 50 | 34 |
| 4 | 25 | 29.5 |
| a | 100 | 26.5 |
| 6 | 75 | 34.5 |
| 6a | 100 | 27 |
| polyaspartic acid | | 37 |

*prepared by the method of Example 1 using 1 equivalent of ammonia

EXAMPLE 11

Maleic anhydride with 99% of a theoretical equivalent of NH$_3$

Maleic anhydride, 39.2 g (0.4 moles) dissolved in 40 g of water was added to 43.1 g of aqueous NH$_4$OH (6.7 g NH$_3$, 0.394 moles) and tumbled at 180°–195° C. for 8 min to give a clear pink melt. It was then heated to 185°–200° C. for 10 min to give a pink foam. The pulverized foam was heated for 10 min at 200°–235° C. to give a pink powder and then heated at 235°–245° C. for 10 min to give 38.5 g of a pink tan powder. The material was hydrolyzed with aqueous NaOH. The GPC gave a peak at 23 min. In the CaSO$_4$ assay of Example 7, the blank was 83 mg while the sample at 2.5 ppm gave a precipitate of 11 mg and at 1.25 ppm it gave a precipitate of 41 mg. In the Kaolin dispersion test of Example 9, at 20 ppm the height of suspended solids was 48 mm whereas the blank was 0 mm.

EXAMPLE 12

Maleic anhydride with 5% of a theoretical equivalent of NH$_3$

Maleic anhydride, 39.2 g (0.4 moles) dissolved in 40 g of water was added to 4.3 g of aqueous NH$_4$OH (0.34 g NH$_3$, 0.02 moles) and tumbled at 180°–195° C. for 12 min to give a tan melt. It was then heated to 200°–225° C. for 10 min to give a tan melt. The melt was heated for 10 min at 220°–230° C. to give 18.1 g of brown solid. The material was hydrolyzed with aqueous NaOH. In the CaSO$_4$ assay of Example 7, the blank was 80 mg while the sample at 2.5 ppm gave a precipitate of 50 mg and at 1.25 ppm it gave a precipitate of 78 mg.

EXAMPLE 13

Preparation of a maleic polymer with a polyamine

To a solution of 1.9 g (0.025 moles) of ethylene diamine in 40 g of water containing 1.0 g of NaOH was added 39.2 g (0.4 moles) of maleic anhydride while stirring at 70°-25° C. for 10 min to give a white slurry of maleic acid. To this slurry was added 21.7 g of water containing 1.7 g (0.1 moles) of ammonia with stirring and cooling. This solution was then heated for 15 min at 170°–200° C. to give a tan melt. The melt was heated at 200°–225° C. for 10 min to give 36.5 g of a tan melt. It was further heated at 225°–235° C. for 10 min to give 35.4 g of tan melt which was not soluble in water.

The powder was dissolved in a solution of 9.0 g of water containing 1.3 g of NaOH to give a clear red-brown solution, estimated to contain 36% solids. In the CaSO$_4$ assay of Example 7, the blank was 80 mg while the sample at 2.5 ppm gave a precipitate of 22 mg and at 1.25 ppm it gave a precipitate of 66 mg. The GPC showed a peak at 29.5 min with a broad shoulder at 21–25 min.

EXAMPLE 14

Preparation of a maleic polymer with maleamic acid

A solution of 9.8 g (0.1 mole) maleic anhydride in 40 g of water was stirred 45 min at 75°-25° C. To this solution was added 34.5 g (0.3 mole) of maleamic acid. The slurry was tumbled at 180°–195° C. for 10 min. All of the solids dissolved to give 39.9 g of a viscous red-tan syrup. Upon further heating for six 10 min periods at 180°–245° C., a tan powder, insoluble in water, was obtained. A 3.9 g portion was dissolved in 10 g of water containing 1.6 g of NaOH. The GPC showed a peak at 22.5 min. In the $CaSO_4$ assay of Example 7, the blank was 86 mg while the sample at 2.5 ppm gave a precipitate of 11 mg.

EXAMPLE 15

Preparation of a maleic polymer with diethylene triamine and oleic acid

A mixture of 2.0 g (0.0175 moles) of diethylene triamine and 1.13 (0.0195 moles) of oleic acid was heated with stirring for 10 min at 190°–210° C. The resulting oil was dissolved in 50 g of methanol. To this solution of 9.8 g (0.1 mole) maleic anhydride in 40 g of water was stirred 45 min at 75°-25° C. To this solution was added 39.0 g (0.4 mole) of maleic anhydride. The reactants were stirred 45 min, following which 4.3 g (0.25 mole) of ammonia in 20 g of water was added (75% of an equivalent). The slurry was tumbled at 170°–185° C. for 10 min. Upon further heating for four 10 min periods at 190°–245° C., 42.3 g of a tan powder, insoluble in water, was obtained. A 4.0 g portion was dissolved in 10 g of water containing 1.6 g of NaOH. The GPC showed two broad peaks at 14 and 24 min. In the $CaSO_4$ assay of Example 7, the blank was 86 mg while the sample at 2.5 ppm gave a precipitate of 8 mg. In the Kaolin dispersion test of Example 9, at 20 ppm the height of suspended solids was 48 mm whereas the blank was 0 mm.

EXAMPLE 16

Preparation of a maleic polymer with oleyl amine

To a solution of 2.67 g (0.01 mole) oleyl amine in 50 g of methanol was added 39.2 g (0.4 mole) maleic anhydride with stirring for 45 min at 25° C., following which 5.0 g (0.29 mole) of ammonia in 20 g of water was added (75% of an equivalent). The slurry was tumbled at 170°–195° C. for 10 min. Upon further heating for four 10 min periods at 200°–235° C., 41.4 g of a brittle glass, insoluble in water, was obtained. The material was dissolved in 100 g of water containing 16 g of NaOH. To this solution was added 5.5 g of 30% $H_2O_2$. After 16 hrs at 25° C., the solution was a clear yellow color. The GPC showed a peak at 14 min. In the $CaSO_4$ assay of Example 7, the blank was 86 mg while the sample at 2.5 ppm gave a precipitate of 9 mg.

It will be apparent to those skilled in the art that the examples and embodiments described herein are by way of illustration and not of limitation, and that other examples may be utilized without departing from the spirit and scope of the present invention, as set forth in the appended claims.

We claim:

1. A polymer produced by a process comprising polymerizing (1) one of the members of the group consisting of maleic acid, malic acid, and fumaric acid, (2) 0.05 equivalents less than one equivalent of ammonia, (3) an amine and (4) a carboxylic acid, at a temperature greater than about 120° C., to produce said polymer.

2. A polymer produced by a process comprising polymerizing (1) one of the members of the group consisting of maleic acid, malic acid, and fumaric acid, (2) less than one equivalent of ammonia, (3) an amine and (4) a carboxylic acid selected from the group consisting of mono and polycarboxylic acids, at a temperature greater than about 120° C., to produce said polymer.

3. A polymer produced by a process comprising polymerizing (1) one of the members of the group consisting of maleic acid, malic acid, and fumaric acid, (2) less than one equivalent of ammonia, (3) an amine and (4) a carboxylic acid selected from the group consisting of alkyl carboxylic acids containing 1–36 carbons, adipic acid, citric acid, fumaric acid, malic acid, malonic acid, succinic acid, glutaric acid, oxalic acid, pimelic acid, itaconic acid, nonanedioic acid, dodecanedioic acid, octanedioic acid, isophthalic acid, terphthalic acid, phthalic acid, stearic acid, oleic acid, N-methyl-N-lauric acid, palmitic acid or an amino acid, at a temperature greater than about 120° C., to produce said polymer.

* * * * *